(12) United States Patent
Rydell

(10) Patent No.: US 6,190,386 B1
(45) Date of Patent: Feb. 20, 2001

(54) ELECTROSURGICAL FORCEPS WITH NEEDLE ELECTRODES

(75) Inventor: Mark A. Rydell, Golden Valley, MN (US)

(73) Assignee: Everest Medical Corporation, Minneapolis, MN (US)

( * ) Notice: Under 35 U.S.C. 154(b), the term of this patent shall be extended for 0 days.

(21) Appl. No.: 09/264,751

(22) Filed: Mar. 9, 1999

(51) Int. Cl.⁷ .................................................... A61B 18/14
(52) U.S. Cl. ................................................. 606/51; 606/50
(58) Field of Search ........................................ 606/50–52

(56) References Cited

U.S. PATENT DOCUMENTS

| | | |
|---|---|---|
| 5,007,908 | 4/1991 | Rydell . |
| 5,083,565 | 1/1992 | Parins . |
| 5,217,460 | 6/1993 | Knoepfler . |
| 5,258,006 | 11/1993 | Rydell et al. . |
| 5,342,359 | 8/1994 | Rydell . |
| 5,445,638 * | 8/1995 | Rydell et al. ........................... 606/51 |

* cited by examiner

*Primary Examiner*—Lee Cohen
(74) *Attorney, Agent, or Firm*—Nikolai, Mersereau & Dietz, P.A.

(57) ABSTRACT

An electrosurgical coagulation instrument specifically designed to be insertable through a cannula for use in coagulating tissue during a laparoscopic or other scope-type procedure. The instrument has both bipolar forceps jaw paddles and bipolar needle electrodes. The needle electrodes are selectively extendable from the distal end of the instrument by manipulation of a knob member in a proximal handle. The needle electrodes can be extended to thereby enter certain tissue such as a tumor to thereby effectuate desiccation thereof and a gradual shrinkage.

7 Claims, 4 Drawing Sheets

ELECTROSURGICAL FORCEPS WITH NEEDLE ELECTRODES

BACKGROUND OF THE INVENTION

This invention relates in general to a bipolar electrosurgical coagulating forceps instrument, and in particular to a bipolar forceps instrument for laparoscopic or other scope-type surgical procedures and having in addition one or more spaced apart needle electrodes which can be selectively extended from the distal end of the instrument.

The benefits of a bipolar electrosurgical instrument are well recognized within the medical profession. In particular, a bipolar instrument provides a physician with greater control of the location of electrical activity within a patient during a surgical procedure. As opposed to a monopolar device, which requires a base plate electrode usually situated at a remote location from the surgery site and therefore requiring passage of current through a portion of the body of the patient, a bipolar device confines electrical activity at the site of the surgical procedure.

Certain treatment procedures are best performed by combining the coagulation of some tissue with a bipolar forceps instrument and a coagulation of other tissue with smaller bipolar electrodes such as needles. For example, a myoma can be treated by first coagulating tissue surrounding the tumor, followed by piercing the tumor with needle electrodes to cause desiccation thereof and a gradual shrinkage.

It is therefore a primary object of the present invention to provide an electrosurgical instrument having functionality as both a bipolar forceps instrument and a bipolar needle electrode instrument.

Another object of the present invention is to provide an electrosurgical instrument for use in laparoscopic or other scope-type procedures and having bipolar forceps jaw or pads and one or more bipolar needle electrodes.

Yet another object of the present invention is to provide an electrosurgical instrument wherein bipolar needle electrodes thereof are selectively extendable and retractable.

These and other objects of the present invention will become apparent throughout the description thereof which now follows.

SUMMARY OF THE INVENTION

The present invention is an electrosurgical coagulation instrument specifically designed to be insertable through a cannula for use in coagulating tissue during a laparoscopic or other scope-type procedure and having both bipolar forceps jaw pads and bipolar needle electrodes which are selectively extendable from the distal end of the instrument as end effectors. The instrument comprises a first elongated, generally rigid outer tube member having a proximal end and a distal end, and a second elongated inner tube member coaxially disposed within the lumen of the first tube member and having a proximal end and a distal end. A pair of electrical conductors are in contact with an electric terminal member at their distal end, and extend longitudinally through the second elongated tube member in side-by-side insulated relationship to terminate distally from the tube member. Opposing first and second conductive pads are secured to the distal ends of the respective first and second conductors to thereby provide forceps jaw pads. One and possibly two electrically conductive wires having proximal ends secured within a longitudinally-slidable, exteriorly accessible knob member extend through the first elongated tube member alongside the second tube member to terminate at their distal ends as needle electrode(s) within electrically conductive chambers or bores of the respective pads. Each of the wire or wire(s) is electrically insulated except at its distal needle end within the bore of the pad. Longitudinal movement distally of the slidable knob member causes the needle end(s) to extend distally beyond the pads.

Opening and closing of the jaw pads comprising the end effectors is accomplished by translational movement of the second elongated tube member to thereby cause its distal end to converge on opposing ramps of each of the conductors. Specifically, each conductor has an uninsulated first zone at its distal end to which the respective pad is attached. Immediately proximal to the first zone is a second insulated zone where each conductor is bent outwardly to form a ramp configuration. A proximally disposed handle means operates to longitudinally advance and retract the second tube member, thereby closing the pad jaws when the second tube member moves distally and opening the pad jaws when the second tube member is thereafter retracted proximally.

In operation, current is supplied to the conductors to thereby activate each of the forceps jaw pads and produce a bipolar instrument. Simultaneously, because of their electrical contact with the pads through the respective electrically conductive bores, the needle electrode(s) is/are likewise activated. When the activated needle electrodes are extended distally by manipulating the knob member, they can be inserted into tissue as indicated to thereby provide treatment. Retracting the needle electrodes into the bores of the pads is accomplished by again manipulating the knob member. After such retraction, the instrument again functions as a bipolar forceps device.

DETAILED DESCRIPTION OF A PREFERRED EMBODIMENT

Figure 1:
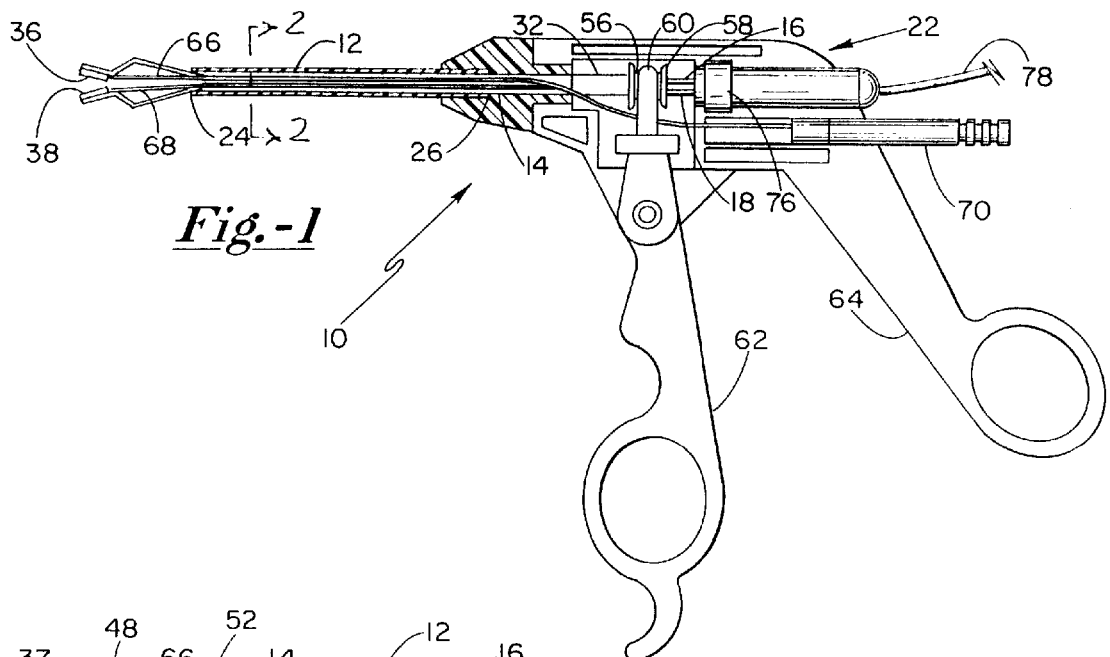
FIG. 1 is a partially sectioned view of an electrosurgical forceps with a pair of needle electrodes.
Figure 3A:
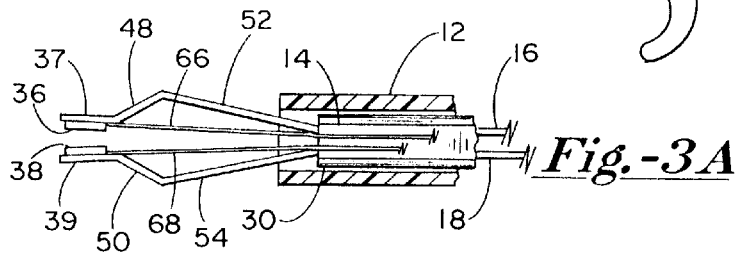
FIGS. 3A–3D are enlarged sectioned elevational views of the distal end of the instrument of FIG. 1 in various operative configurations.
Figure 2:
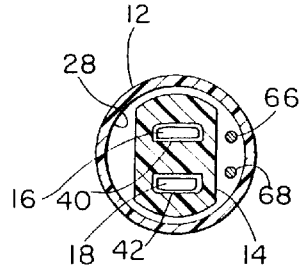
FIG. 2 is a cross section view along line 2—2 of FIG. 1.
Figure 3B:
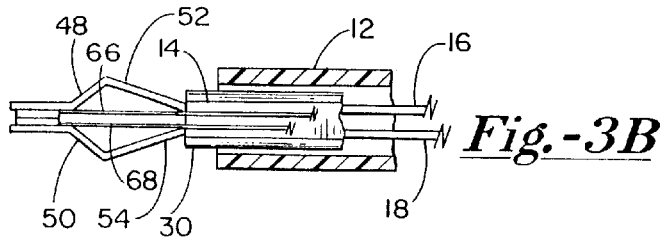
Figure 3C:
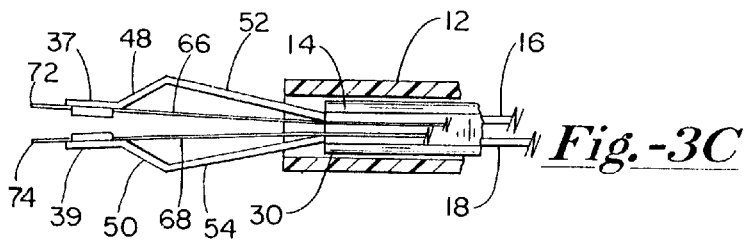
Figure 3D:
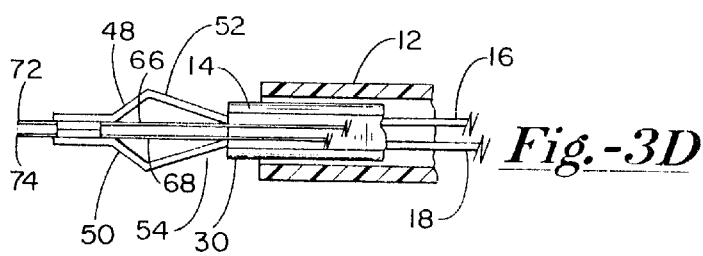

FIG. 1 shows a bipolar electrosurgical coagulating forceps instrument 10 designed for use in percutaneous laparoscopic or other scope-type surgical procedures. As illustrated in FIGS. 1 and 2, the instrument 10 generally comprises an elongated, rigid outer tube member 12, an elongated semi rigid inner tube member 14 having flat sides, a first electrical conductor 16, a second electrical conductor 18, and a plastic scissors-type handle member indicated generally by numeral 22. The outer tube member 12, preferably constructed from stainless steel or glass fiber reinforced plastic, has a distal end 24, a proximal end 26 held by friction fit in the handle 22, and a lumen 28 through which the inner tube member 14 coaxially passes. The inner tube member 14 is preferably constructed from an insulating material such as nylon or polyurethane, and has a distal end 30 and a proximal end 32. The outside diameter of the inner tube member 14 is small enough to fit loosely inside the lumen 28 of the outer tube member 12, thereby allowing translational movement within the outer tube member 12. The outside diameter of the outer tube member 12 is small enough to pass through a cannula, and its length is sufficient to reach a surgical site. The distal end 30 of the inner tube member 14 generally aligns with or is slightly recessed with respect to the distal end 24 of the outer tube member 12 when forceps jaw pads 36, 38 are open relative to one another (FIGS. 3A and 3C) and protrudes distally beyond the distal end 24 of the outer tube member 12 when the pads 36, 38 are closed (FIGS. 3B and 3D). As shown in FIGS. 1–3, electrical conductors 16, 18 extend the length of the inner tube member 14 through respective first and second lumens, 40, 42. The lumens 40, 42 are electrically insulated from each other. The respective distal ends of the conductors 16, 18 have respective first zones 48, 50 which are free of electrical insulation and to which electrically conductive first and second forceps jaw pads 36, 38 are welded. Immediately proximal the first zones 48, 50 of the conductors 16, 18 are respective insulated second zones 52, 54 where the conductors 16, 18 are bent away from each other to create respective ramp surfaces engageable by the distal end 30 of the inner tube member 14. When the inner tube member 14 is moved distally inside the lumen 28 of the outer tube member 12, the inner tube member 12 slides over the conductors 16, 18 to thereby exert pressure on the ramp surfaces and close the pads 36, 38. Reversing the procedure permits the pads 36, 38 to open. The respective proximal ends of the conductors 16, 18 are in contact with an electrical connector 76 within the handle member 22 and in communication via an electrical cord 78 with a high frequency generator (not shown).

Movement of the inner tube member 12 to actuate the end effectors is accomplished by displacing a slidable spool 56 located inside the handle 22. Specifically, the proximal end 32 of the inner tube member 14 extends proximally from the proximal end 26 of the outer tube member 12 to be molded to the spool 56 by an insert molding operation. The spool has two end flanges 58 between which resides a tab 60 extending from a movable arm 62 pivotally mounted to a stationary arm 64 of the handle 22. When the arm 62 is manipulated, the tab 60 impinges against either flange 58, depending on the direction of movement of the arm 62, to thereby move the inner tube member 14 and resultantly open or close the jaw pads 36, 38. As is evident in FIG. 1, the handle 22 is configured in a scissors style to thereby be comfortably manipulated by an operator.

As seen in FIG. 1, an electrically conductive first wire 66 and an electrically conductive second wire 68 extend from an electrically insulated plastic slidable knob member 70 in which the respective proximal ends of the wires 66, 68 are imbedded. The first and second wires 66, 68 extend through the lumen 28 of the outer tube member 12 alongside the inner tube member 14 to terminate as first and second needle electrodes 72, 74 within respective first and second electrically conductive bores 37, 39 formed through the respective pads or formed a length of tubing disposed on the outer surfaces of the respective first and second pads 36, 38.

Figure 5:
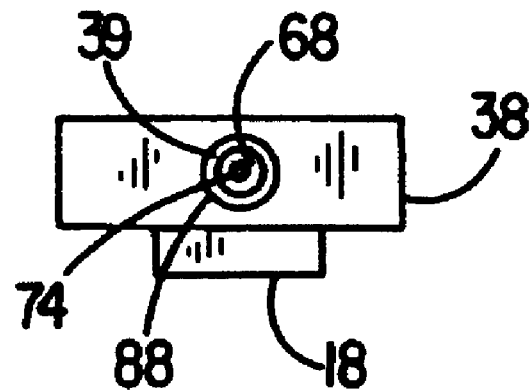
FIG. 5 is a cross section view along line 5—5 of FIG. 4A.

FIG. 5 illustrates the pad 38 attached to the distal end of first conductor 18, and shows the bore 39 with the needle electrode 74 therein. First and second bores 37, 39 may further include an insulating sleeve 88 to prevent electrical contact between first and second needle electrodes 72, 74 and the metal pad material.

As is apparent, when the instrument 10 is energized, current flows through the conductors 16, 18 to the pads 36, 38. Because the bores 37, 39 are electrically conductive, current likewise flows thereto and continues to the needle electrodes 72, 74. Sliding the knob member 70 distally causes distal movement of the wires 66, 68 to thereby extend the needle electrodes 72, 74 distally through the bores 37, 39 and beyond the pads 36, 38. In this manner, bipolarity is established between the needle electrodes 72, 74.

In operation, the instrument 10 functions as a coagulating forceps instrument when the needle electrodes 72, 74 are retracted to be disposed within the respective bores 37, 39. This configuration permits a physician to coagulate readily accessible tissue. Manipulation of the knob member 70 in a distal direction extends the needle electrodes 72, 74 beyond the distal end of the pads 36, 38 to permit coagulation of tissue such as inner tissue of a tumor which is not readily accessible to a forceps jaw pad. FIGS. 3A–3D illustrate that the pads 36, 38 may be open or closed while the needle electrodes 72, 74 are extended or retracted. Thus, the single instrument 10 permits an operator to coagulate different types and locations of tissue with a single instrument.

In the embodiment illustrated in FIGS. 1–3 of the drawings, two needle electrodes are deployable relative to the clamping jaws of the instrument. FIGS. 4A–4D and FIG. 6 illustrate an alternative embodiment in which only a single needle electrode is utilized. Because the handle mechanism shown in FIG. 1 is easily modified to accommodate a single needle electrode, only the distal end portion of the instrument is illustrated in FIGS. 4A–4D.

Figure 4A:
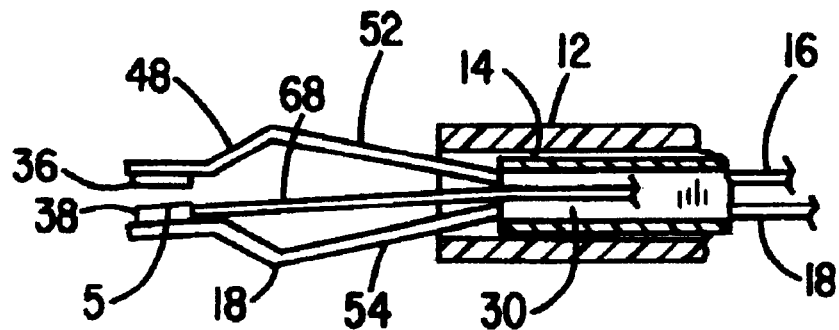
FIGS. 4A–4D is a partially sectioned elevational view of an electrosurgical forceps, except with only a single needle electrode extended.

In FIG. 4A, the inner tube 30 is shown as being retracted relative to the ramps 52 and 54 and, accordingly, the forceps pads 36 and 38 are open relative to one another. The wire 68 leading to the needle electrode 74 is also retracted such that the needle electrode 74 is contained within the confines of the bore 39 (FIG. 5). In the second embodiment, the bore 39 also includes an insulating sleeve 88 (FIG. 5) preventing electrical contact between instead the needle electrode 74 and the metal pad material 38.

Figure 4B:
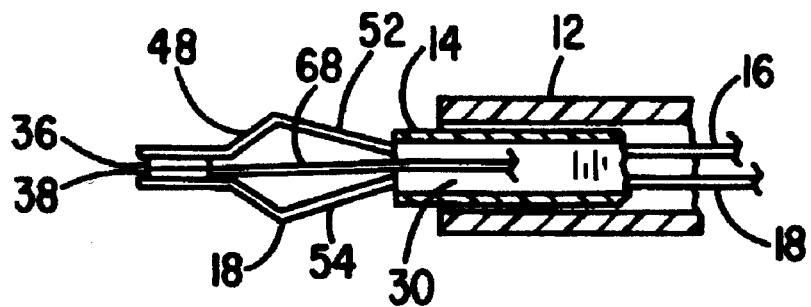

In FIG. 4B, the scissors handle has been manipulated so as to cause the distal end 30 of the inner tube 14 to engage the ramps 52 and 54 so as to close the jaws 36–38 relative to one another. The handle 70 shown in FIG. 1 has not, as yet, been advanced in the distal direction to deploy the needle electrode.

Figure 4C:
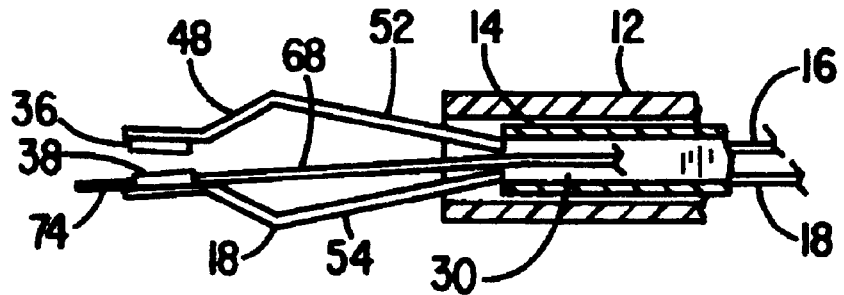
Figure 4D:
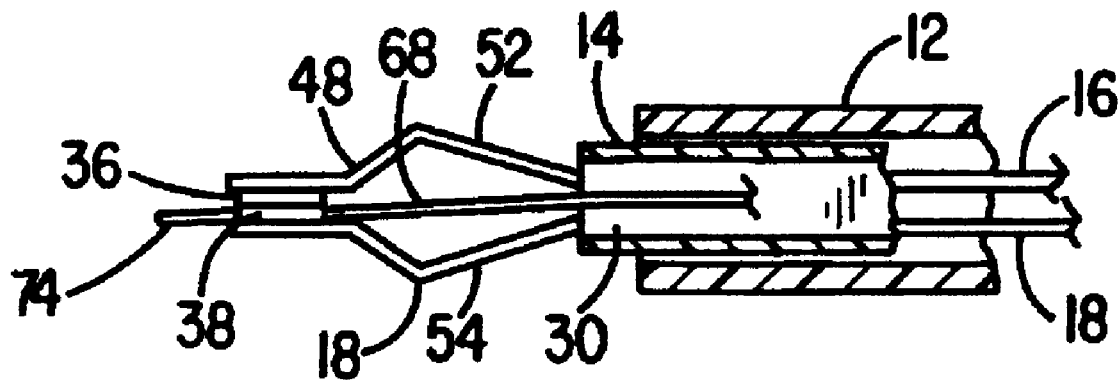

FIGS. 4C–4D illustrate that the needle electrode 74 can be deployed irrespective of whether the jaws of the forceps are open or closed.

Figure 6:
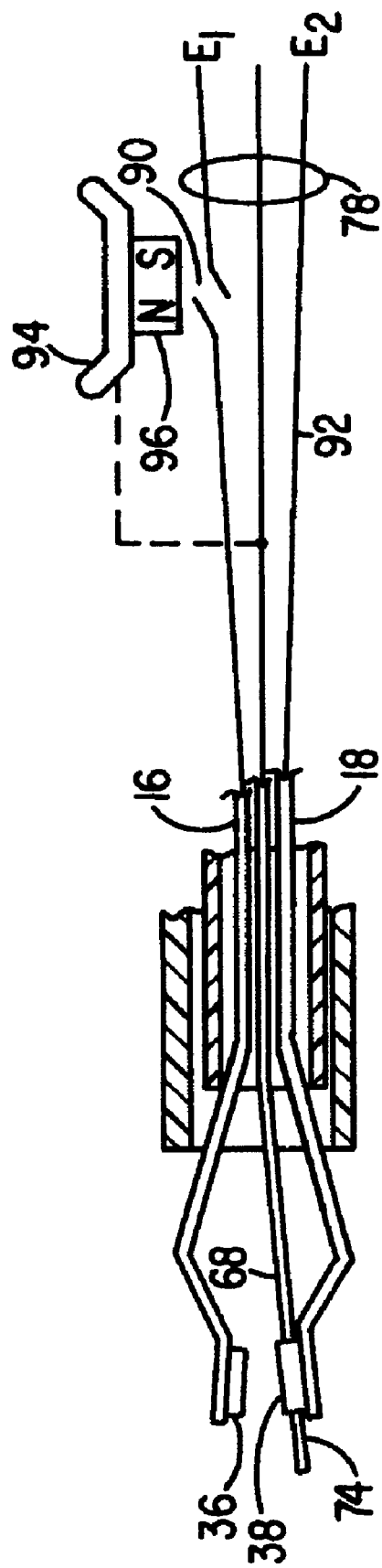
FIG. 6 is a partial mechanical/electrical schematic diagram of a single needle electrode embodiment of the invention.

FIG. 6 is a partial schematic electrical diagram showing the manner in which electrical energy is applied to the forceps pads 36–38 and to the needle electrode 74. In this drawing, the cord 78 is connected to an electrosurgical generator providing a voltage $E_1$ to the wire 20 and, therefore, to the needle electrode 19 to which conductor 20 connects. The voltage terminal $E_1$ is also connected through a magnetic reed switch 90 to the electrical conductor 16 leading to the forceps jaw pad 36. The voltage terminal $E_2$ is connected via conductor 92 to electrical conductor 18 to which the forceps jaw pad 38 attaches. A thumb slide 94 having a permanent magnet 96 affixed to it is mechanically coupled to the wire 68. The thumb slide 94 is appropriately mounted on the handle 22 in proximity to the reed switch 90. When the thumb slide 94 is in its proximal-most position, the needle electrode 74 is contained within the insulating tube 88 contained within the pad member 38. Also, at this time, the magnet 96 is sufficiently remote from the switch 90 that its contacts are closed so that the voltage $E_1$ is applied to the pad member 36, via electrical conductor 16. However, when the thumb slide 94 is moved in the distal direction, the needle electrode 19 is deployed beyond the distal end of the pad 38 and, simultaneously, the reed switch 90 is actuated by the permanent magnet 96, opening its contacts and removing the power from the pad 36. When the jaws are open relative to one another and the needle electrode 19 is deployed, a voltage difference exists between the needle electrode and pad 38 surrounding it allowing bipolar electrosurgical cutting to occur. Even with the jaws closed relative to one another, as shown in FIG. 4D, there will be no short circuit between the pads 36 and 38 because of the open contacts of the reed switch 90 and the voltage is still maintained between the needle electrode 74 and both of the forceps pads 36 and 38.

While an illustrative and presently preferred embodiment of the invention has been described in detail herein, it is to be understood that the inventive concepts may be otherwise variously embodied and employed and that the appended claims are intended to be construed to include such variations except insofar as limited by the prior art.

What is claimed is:

1. A bipolar electrosurgical coagulation instrument comprising:
   (a) a first tube member having a proximal end and a distal end;
   (b) a second tube member coaxially disposed within the lumen of the first tube member and having a proximal end and a distal end;
   (c) a first conductor and a second conductor, said first and second conductors extending longitudinally through the second tube member in side-by-side relation and insulated from one another along the length thereof, each of said conductors having a proximal end and a distal end, said distal end of each of said conductors being free of insulation over a first predetermined zone, the distal ends of said conductors in said first zone being in parallel, face-to-face relation with respect to one another, with the first conductor having secured thereto a first pad forming a first forceps jaw and the second conductor having secured thereto a second pad forming a second forceps jaw, said conductors each including a second zone, proximal and contiguous to the first zone, in which said conductors are bent to create a ramp surface selectively engageable by the distal end of the second tube member when the second tube member is translated in the distal direction within the lumen of the first tube member;
   (d) an electrically conductive first wire and an electrically conductive second wire extending from an electrically insulated, exteriorly-accessible, movable knob member through the lumen of the first tube member alongside the second tube member to respectively terminate as a first needle electrode within a first electrically conductive bore disposed in the first pad and a second needle electrode within a second electrically conductive bore disposed in the second pad; and
   (e) a handle means operatively coupled to the proximal end of the first tube member, the proximal end of the second tube member, and the proximal ends of the conductors for translational, longitudinal, reciprocal motion to the second elongated tube member within the lumen of the first tube member without displacing said conductors; and
   (f) means for delivering high frequency energy to the first and second conductors.

2. A bipolar electrosurgical coagulation instrument as claimed in claim 1 wherein the second tube member has opposing flat sides.

3. A bipolar electrosurgical coagulation instrument as claimed in claim 2 wherein the second tube member has therein two lumens electrically insulated from each other and wherein the first and second conductors respectively reside.

4. A bipolar electrosurgical coagulation instrument as claimed in claim 1 wherein the handle means comprises a scissors-style handle having a movable arm and a stationary arm, whereby movement of the movable arm effectuates motion to the second tube member.

5. A bipolar electrosurgical coagulation instrument, comprising:
   (a) an elongated, generally rigid tube member having a proximal end and a distal end with a lumen extending therebetween;
   (b) first and second end effectors disposed at the distal end of the tube member, each with a conductive pad forming a forceps jaw, each of the conductive pads including a longitudinal bore therethrough;
   (c) a manually operable handle member affixed to the proximal end of the tube member;
   (d) means actuated by the handle member and cooperating with the end effectors for opening and closing the forceps jaws relative to one another;
   (e) first and second conductors extending from the handle member through the lumen of the tube member and electrically connectable to the conductive pads for applying a voltage between the conductive pads on the first and second end effectors;
   (f) a first needle electrode slidable within the longitudinal bore of the conductive pad on the first end effector;
   (g) a manually operable slide member on the handle member, operatively coupled to the first needle electrode, for effecting extension and retraction of the first needle electrode relative to a distal end of the conductive pad on the first end effector; and
   (h) means for selectively applying a voltage between the first and second conductors or between the first conductor and the first needle electrode.

6. The bipolar surgical coagulation instrument as in claim 5 wherein the handle member comprises a scissors style handle having a movable arm and a stationary arm, the movable arm being operatively engaged with the first and second end effectors for opening and closing the forceps jaws relative to one another, the stationary arm supporting the proximal end of the tube member.

7. The bipolar electrosurgical coagulation instrument as in claim 5 wherein the means for selectively applying a voltage comprises an electrical switch actuated by movement of the manually operable slide member.

* * * * *